United States Patent
Laudon et al.

(10) Patent No.: US 10,722,494 B2
(45) Date of Patent: Jul. 28, 2020

(54) MELATONIN MINI-TABLETS AND METHOD OF MANUFACTURING THE SAME

(71) Applicant: NEURIM PHARMACEUTICALS LTD., Tel Aviv (IL)

(72) Inventors: Moshe Laudon, Tel Aviv (IL); Nava Zisapel, Tel Aviv (IL)

(73) Assignee: Neurim Pharmaceuticals Ltd., Tel Aviv (IL)

(*) Notice: Subject to any disclaimer, the term of this patent is extended or adjusted under 35 U.S.C. 154(b) by 0 days.

(21) Appl. No.: 16/176,338

(22) Filed: Oct. 31, 2018

(65) Prior Publication Data

US 2019/0060277 A1 Feb. 28, 2019

Related U.S. Application Data

(63) Continuation of application No. PCT/IB2016/057190, filed on Nov. 29, 2016.

(60) Provisional application No. 62/415,014, filed on Oct. 31, 2016.

(51) Int. Cl.
*A61K 31/4045* (2006.01)
*A61K 9/20* (2006.01)
*A61P 25/20* (2006.01)

(52) U.S. Cl.
CPC ........ *A61K 31/4045* (2013.01); *A61K 9/2009* (2013.01); *A61K 9/2018* (2013.01); *A61K 9/2027* (2013.01); *A61K 9/2072* (2013.01); *A61P 25/20* (2018.01)

(58) Field of Classification Search
None
See application file for complete search history.

(56) References Cited

U.S. PATENT DOCUMENTS

| | | | |
|---|---|---|---|
| 4,600,723 A | 7/1986 | Short et al. | |
| 5,449,683 A | 9/1995 | Wurtman | |
| 5,498,423 A | 3/1996 | Zisapel | |
| 5,500,225 A | 3/1996 | Laudon et al. | |
| 5,750,557 A | 5/1998 | Zisapel | |
| 6,048,888 A | 4/2000 | Zisapel | |
| 6,242,004 B1* | 6/2001 | Rault | A61K 9/006 424/434 |
| 6,469,044 B1 | 10/2002 | Zisapel | |
| 2001/0038863 A1* | 11/2001 | Jaenicke | A61K 36/77 424/725 |
| 2004/0228830 A1* | 11/2004 | Hirsh | A61K 9/5026 424/78.12 |
| 2004/0248966 A1 | 12/2004 | Zisapel | |
| 2005/0175692 A1 | 8/2005 | Zisapel | |
| 2006/0229340 A1 | 10/2006 | Zisapel | |
| 2008/0085317 A1 | 4/2008 | Zisapel et al. | |
| 2008/0175910 A1* | 7/2008 | Andre | A61K 9/5078 424/472 |
| 2009/0175936 A1 | 7/2009 | Rohr | |
| 2010/0120887 A1 | 5/2010 | Terman et al. | |
| 2012/0195968 A1 | 8/2012 | Shaw et al. | |
| 2015/0157604 A1* | 6/2015 | Morozova | A61K 31/4045 514/415 |
| 2016/0243038 A1 | 8/2016 | Shah et al. | |

FOREIGN PATENT DOCUMENTS

| | | |
|---|---|---|
| AU | 2002326114 B2 | 3/2003 |
| EP | 0518468 A1 | 12/1992 |
| EP | 0724878 A2 | 8/1996 |
| EP | 2949322 A1 | 12/2015 |
| WO | 95/03043 A1 | 2/1995 |
| WO | 03/086352 A1 | 10/2003 |
| WO | 2005063297 A2 | 7/2005 |

OTHER PUBLICATIONS

International Search Report cited in PCT/IB2016/057190 dated Feb. 15, 2017, 14 pages.
Spomer, N., et al., "Acceptance of uncoated mini-tablets in young children: results from a prospective exploratory cross-over study" Arch. Dis. Child., 2012; vol. 97: No. 3, pp. 283-286.
Stoltenberg et al., "Orally disintegrating mini-tablets (ODMTs) A novel solid oral dosage form for paediatric use", European Journal of Pharmaceutics and Biopharmaceutics, vol. 78, No. 3, 2011, pp. 462-469.
Gringras et al., "Efficacy and Safety of Pediatric Prolonged-Release Melatonin for Insomnia in Children with Autism Spectrum Disorder", Journal of the American Academy of Child & Adolescent Psychiatry, 2017; 56(11): 948-957.
Shah, "Dissolution: A Quality Control Test vs. A Bioequivalence Test", Dissolution Technologies, Nov. 2001, 2 pages.
Examination report No. 1 cited in Australian Application No. 2016426598 dated Jun. 6, 2018, 4 pages.
Notice of Acceptance for patent application in Australian Application No. 2016426598 dated Oct. 22, 2018, 3 pages.
Schrier L. et al., Chapter 8: Pharmacokinetics of prolonged-release melatonin mini-tablets in children with both autism spectrum disorder and a sleep disorder, Non-invasive monitoring of pharmacokinetics and pharmacodynamics for pharmacological drug profiling in children and adolescents, Universiteit Leiden, pp. 213 to 240, 2015.
A randomized, placebo-controlled study to investigate the efficacy and safety of Circadin® to alleviate sleep disturbances in children with neurodevelopmental disabilities, Clinical Study Protocol No. NEU_CH_7911, Phase III, Version 6.0, 2015, Amendment 5, pp. 1 to 119.

(Continued)

*Primary Examiner* — James W Rogers
(74) *Attorney, Agent, or Firm* — Rothwell, Figg, Ernst & Manbeck, P.C.

(57) ABSTRACT

The instant invention is generally directed to a patient-friendly drug delivery system for targeted populations, such as pediatric and geriatric patients. Specifically, the present invention relates to a pharmaceutical composition in the form of mini-tablets. Even more specifically, the present invention relates to a pharmaceutical composition comprising a therapeutically-effective amount of melatonin in the form of mini-tablets.

7 Claims, 1 Drawing Sheet

(56) References Cited

OTHER PUBLICATIONS

Circadin® (melatonin) CHMP assessment report for paediatric use studies submitted according to Article 46 of the Regulation (EC) No. 1901/2006, Procedure No. EMA/H/C/695/P46/019, European Medicines Agency, dated Dec. 18, 2014 (published Feb. 13, 2015).
Krakowiak, P. et al., 'Sleep problems in children with autism spectrum disorders, developmental delays, and typical development: a population-based study', Journal of Sleep Research (2008) 17(2) 197-206.
Pillar, J. et al., 'Melatonin Improves Sleep-Wake Patterns in Psychomotor Retarded Children', Pediatric Neurology (2000) 23(3) 225-8.
Souders M.C. et al., 'Sleep Behaviors and Sleep Quality in Children with Autism Spectrum Disorders', Sleep (2009) 32(12) 1566-78.
Doo S. et. al., 'Sleep problems of children with pervasive developmental disorders: correlation with parental stress', Developmental Medicine & Child Neurology (2006) 48 650-5.
Phillips L. et al., 'Systematic review of melatonin treatment in children with neurodevelopmental disabilities and sleep impairment', Developmental Medicine & Child Neurology (2004) 46 771-5.
Assessment Report for Circadin, Procedure No. EMEA/H/C/695, European Medicines Agency, Nov. 7, 2007, 52 pages.
Carr, M.B. et al., 'Long-term effectiveness outcome of melatonin therapy in children with treatment-resistant circadian rhythm sleep disorders', Journal of Pineal Research (2007) 43 351-9.
Jan, J.E. et al., 'Clinical trials of controlled-release melatonin in children with sleep-wake cycle disorders', Journal of Pineal Research (2000) 29 34-9.
De Leersnyder, H. et al., 'Prolonged-Release Melatonin for Children With Neurodevelopmental Disorders', Pediatric Neurology (2011) 45 23-6.
De Leersnyder, H. et al., 'β1-adrenergic antagonists and melatonin reset the clock and restore sleep in a circadian disorder, Smith-Magenis syndrome', Journal of Medical Genetics (2003) 40 74-8.
Giannotti, F. et al., 'An Open-Label Study of Controlled-Release Melatonin in Treatment of Sleep Disorders in Children with Autism', Journal of Autism and Developmental Disorders (2006) 36 741-52.
Shah, T. et al., 'Administration of melatonin mixed with soft food and liquids for children with neurodevelopmental difficulties', Developmental Medicine & Child Neurology (2008) 50 845-9.
Miano, S. et al., 'Epidemiology and Management of Insomnia in Children with Autistic Spectrum Disorders', Paediatric Drugs (2010) 12(2) 75-84.
Garstang, J. et al, 'Randomized controlled trial of melatonin for children with autistic spectrum disorders and sleep problems', Child: care, health and development (2006) 32(5) 585-9.
Wasdell, M.B. et al., 'A randomized, placebo-controlled trial of controlled release melatonin treatment of delayed sleep phase syndrome and impaired sleep maintenance in children with neurodevelopmental disabilities', Journal of Pineal Research (2008) 44 57-64.
Van Geijlswijk, I.M. et al., 'Evaluation of sleep, puberty and mental health in children with long-term melatonin treatment for chronic idiopathic childhood sleep onset insomnia', Psychopharmacology (2011) 216 111-20.
Arendt, J., 'Melatonin, Circadian Rhythms, and Sleep', The New England Journal of Medicine (2000) 343(15) 1114-6.
Bunn, J., 'Melatonin and its use in children', The Pharmaceutical Journal (2013) 290 147-9.

Depreux, J. et al, 'Synthesis and Structure-Activity Relationships of Novel Naphthalenic and Bioisosteric Related Amidic Derivatives as Melatonin Receptor Ligands', Journal of Medicinal Chemistry (1994) 37(20) 3231-9.
Lynch, H.J. et al., 'Daily Rhythm in Human Urinary Melatonin', Science (1975) 187(4172), 169-71.
Ali, A.A. et al., 'Pediatric drug development: formulation considerations', Drug Development and Industrial Pharmacy (2014) 40(10) 1283-99.
Van Riet-Nales, D.A. et al., 'Safe and effective pharmacotherapy in infants and preschool children: importance of formulation aspects' Archives of Disease in Childhood (2016) 101 662-9.
Yue Teng and Zhihui Qiu, 'Fluid bed coating and granulation for CR delivery', Chapter 8,115-128, Oral Controlled Release Formulation Design and Drug Delivery: Theory to Practice, Edited by Hong Wen and Kinam Park (2010) Wiley.
'In Vitro Dissolution Testing for Solid Oral Dosage Forms', Technical Brief (vol. 5, 2010), Particle Sciences Drug Development, Manufacturing & Delivery Services.
Thomson, S.A. et al., 'Minitablets: New Modality to Deliver Medicines to Preschool-Aged Children', Pediatrics (2009) 123(2) e235-8.
Spomer, N. et al., 'Acceptance of uncoated mini-tablets in young children: results from a prospective exploratory cross-over study', Archives of Disease in Childhood (2012) 97(3), 283-6.
Chua, H.M. et al., 'Dissolution of Intact, Divided and Crushed Circadin Tablets: Prolonged vs. Immediate Release of Melatonin', Pharmaceutics (2016) 8(1) 1-11.
Product Information Circadin® Prolonged Released Tablets, dated Jun. 9, 2016, 13 pages.
Eudragit technical information, Jul. 2015 7 pages.
Jannat E. et al., 'Granulation Techniques & Its Updated Modules', The Pharma Innovation Journal (2016) 5(10) 134-141.
Brusco L.I. et al., 'Effect of Melatonin in Selected Populations of Sleep-Disturbed Patients', Biological Signals Receptors (1999) 8 126-131.
Garfinkel D. et al., 'Improvement of sleep quality in elderly people by controlled-release melatonin', The Lancet (1995) 346(8974) 541-544.
Haimov I. et al., 'Melatonin Replacement Therapy of Elderly Insomniacs', Sleep (1995) 18(7) 598-603.
Lemoine P. et al., 'Prolonged-release formulation of melatonin (Circadin) for the treatment of insomnia', Expert Opinion on Pharmacotherapy (2012) 13(6) 895-905.
Benloucif S. et al., 'Measuring Melatonin in Humans', Journal of Clinical Sleep Medicine (2008) 4(1) 66-69.
Zhdanova I.V. et al., 'Endogenous Melatonin Levels and the Fate of Exogenous Melatonin: Age Effects', Journal of Gerontolog, (1998) 53A(4) B293-B298.
Zhdanova I.V. et al., 'Melatonin: A Sleep-Promoting Hormone', Sleep (1997) 20(10) 899-907.
Aleksovski A. et al., 'Mini-tablets: a contemporary system for oral drug delivery in targeted patient groups', Expert opinion on Drug Delivery (2014) 12(1) 1-20.
Narayana Raju P. et al., 'Effect of Tablet Surface Area and Surface Area/Volume on Drug Release from Lamivudine Extended Release Matrix Tablets', International Journal of Pharmaceutical Sciences and Nanotechnology (2010) (3)1 872-6.
First Examination Report cited in Australian Application No. 2019200479 dated Oct. 10, 2019, 4 pages.
First Examination Report cited in New Zealand Application No. No. 747702 dated Jul. 4, 2019, 7 pages.
Communication pursuant to Article 94(3) EPC cited in corresponding European Application No. 16 805 903.8-1114 dated Dec. 9, 2019, 6 pages.

\* cited by examiner

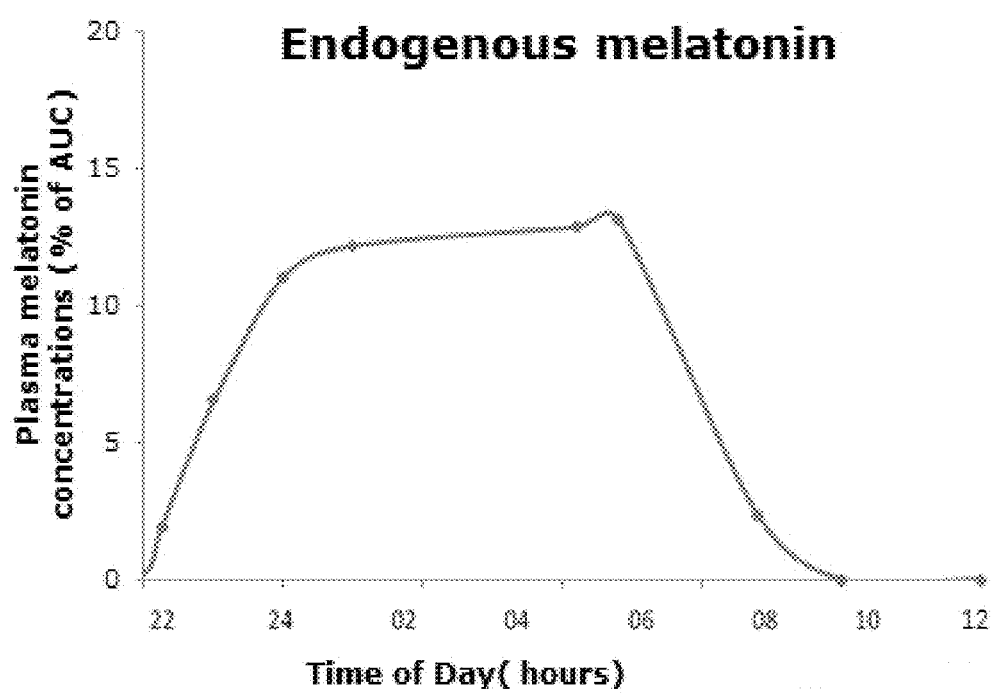

MELATONIN MINI-TABLETS AND METHOD OF MANUFACTURING THE SAME

CROSS REFERENCE TO RELATED APPLICATION

This application is a continuation of PCT/IB2016/057190, filed Nov. 29, 2016, which claims the benefit of U.S. Provisional Application No. 62/415,014 filed on Oct. 31, 2016, the disclosures of which are incorporated herein in their entirety by reference.

FIELD OF THE INVENTION

The present invention is generally directed to a patient-friendly drug delivery system for targeted populations, such as pediatric and geriatric patients.

BACKGROUND OF THE INVENTION

The goal of any drug delivery system is to provide a therapeutic amount of drug to the proper site in the body to achieve and then maintain the desired drug concentration. The most convenient and commonly employed route of drug delivery has historically been by solid oral dosage forms, particularly tablets and capsules. However, conventional tablets and capsules are limited by their rigid dose content. Furthermore, difficulty swallowing tablets and capsules is a problem for many patients, and can lead to a variety of adverse events and patient noncompliance with treatment regimens.

Melatonin is an indole-derived hormone produced at night by the pineal gland, and it plays a major physiological role in the regulation of sleep. Melatonin is produced and secreted into the plasma in a circadian rhythm which parallels the sleep-wake cycle. Exogenous melatonin is often administered as a sleep-aid. Melatonin is also used to treat dependence on, tolerance of, or addiction to a benzodiazepine, as described in U.S. Pat. No. 6,469,044, the disclosure of which is incorporated herein by reference in its entirety. Treatment with melatonin has been shown to produce positive effects on sleep induction, sleep quality, and most importantly, day-time-functioning as well as quality of life. Melatonin use is not associated with development of dependency.

Melatonin is available in several solid oral dosage forms, particularly tablets and capsules. Existing melatonin oral dosage forms include immediate-release dosage forms, useful for treating delayed sleep onset, and prolonged release forms, useful for sleep maintenance. Oral absorption of melatonin is rapid and peak plasma levels are achieved 20 to 60 min following ingestion.

Existing melatonin products suffer from disadvantages including poor patient compliance issues due to difficulty in swallowing tablets, e.g., prolonged-release Circadin® tablets, which are about 8.1 mm in diameter and 3-5 mm thick. Due to these difficulties, some patients break, crush, or chew the prolonged-release Circadin® tablets, which results in loss of its prolonged-release profile. As such, when Circadin® tablets are broken, crushed or chewed, they exhibit a release profile that is close to immediate-release melatonin.

There exists a need in the art for improved drug delivery systems for use in patient populations having an inability to swallow tablets and capsules, e.g., pediatric and geriatric populations. Specifically, there exists a need in the art for novel mini-tablet formulations. Even more specifically, there exists a need in the art for novel melatonin mini-tablet formulations having precise pharmacologic and pharmacokinetic properties.

BRIEF SUMMARY OF THE INVENTION

The present disclosure is generally directed to a patient-friendly drug delivery form and system for patients that have difficulty swallowing melatonin oral dosage forms intact.

In one embodiment, the present disclosure relates to a melatonin mini-tablet that contains a therapeutically effective amount of melatonin and one or more pharmaceutically acceptable carriers, wherein the mini-tablet has a diameter of less than or equal to 4 mm.

Another embodiment of the invention relates to a method of manufacturing a melatonin mini-tablet, the method comprising combining a therapeutically effective amount of melatonin and one or more pharmaceutically acceptable carriers to produce a mixture, and compressing the mixture into mini-tablets that each have a diameter of less than or equal to 4 mm.

The instant invention also relates to a method of inducing sleep in a patient in need thereof, the method comprising orally administering to the patient a pharmaceutical mini-tablet comprising a therapeutically effective amount of melatonin, wherein sleep is induced in the patient. Additionally, the invention relates to a method of orally administering melatonin to a patient who has difficulty swallowing tablets, the method comprising orally administering to the patient a pharmaceutical mini-tablet comprising a therapeutically effective amount of melatonin.

The invention further relates to a pharmaceutical mini-tablet formulation comprising melatonin in combination with at least one pharmaceutical carrier, diluent or coating, wherein, upon administration to a human, the formulation releases melatonin over time such that the person's melatonin plasma profile substantially simulates the melatonin plasma profile of a human having a normal endogenous melatonin profile.

In certain embodiments, the invention further relates to a pharmaceutical formulation containing a plurality of mini-tablets containing melatonin. In certain embodiments, the plurality of mini-tablets in the pharmaceutical formulation is a combination of immediate release and controlled-release mini-tablets. In other embodiments, each of the plurality of mini-tablets in the pharmaceutical formulation is a controlled-release mini-tablet. In other embodiments, each of the plurality of mini-tablets in the pharmaceutical formulation is an immediate-release mini-tablet provided in the form of a pharmaceutical formulation that has a controlled-release profile, e.g., in a controlled release capsule.

Further embodiments of the invention comprise a method of inducing sleep in a patient in need thereof, the method comprising manufacturing a melatonin mini-tablet, and orally administering to the patient a pharmaceutical mini-tablet comprising a therapeutically effective amount of melatonin.

These and other embodiments of the invention will be described in further detail below.

BRIEF DESCRIPTION OF THE DRAWINGS

FIG. 1 is a plot of endogenous melatonin plasma levels (adapted from Arendt et al, J Clin Endocrinol Metab. 1985; 60(6): 1166-73. 1985).

DETAILED DESCRIPTION OF THE INVENTION

Mini-tablets according to the present disclosure satisfy long-felt, but unmet therapeutic needs to provide effective melatonin therapy to a patient suffering from impaired swallowing and/or undergoing polypharmacy therapy. A problem with existing melatonin oral dosage, either immediate-release dosage forms or prolonged-release dosage forms, is that they are difficult to swallow for some patients. As such, existing melatonin products suffer from disadvantages including patient compliance issues due to difficulty in swallowing tablets, e.g., prolonged-release Circadin® tablets, which are about 8.1 mm in diameter and 3-5 mm thick. Due to these difficulties, some patients break, crush, or chew the prolonged-release Circadin® tablets, which results in loss of its prolonged-release profile. As such, when Circadin® tablets are broken, crushed or chewed, they exhibit a release profile that is close to immediate-release melatonin. Due to these problems, before the present invention, there was a long-felt, but unmet need for a prolonged-release dosage form of melatonin with improved swallowing, flexible dosing, and better patient compliance. The present disclosure satisfies the need in the field by providing melatonin mini-tablets having improved swallowing, flexible dosing, and better patient compliance, as well as a controlled-release profile that achieves the same minimal blood levels of melatonin present at night in the brain of a human with a normal endogenous melatonin profile, shown in FIG. 1, as well as an acceptable safety profile.

Mini-tablets according to the present disclosure provide pharmacokinetic and pharmacodynamics properties such that a patient achieves a minimal blood level of about 60 to about 200 picograms melatonin per milliliter over at least four hours following the administration without suffering unacceptable side effects. In certain embodiments, mini-tablets according to the present disclosure provide pharmacokinetic and pharmacodynamics properties such that a patient achieves a minimal blood level of about 100 to about 200 picograms melatonin per milliliter over at least four hours following the melatonin administration without suffering unacceptable side effects.

In certain embodiments, the mini-tablets will release less than 50% of the active pharmaceutical ingredient within 1 hour of oral administration. In certain embodiments, the mini-tablets will release about greater than 70% of the active pharmaceutical ingredient within 6 hours of oral administration.

Mini-tablets also offer therapeutic benefits such as dose flexibility. Mini-tablets are flat or slightly curved tablets with a diameter less than 4.0 mm. Mini-tablets are particularly suitable for polypharmacy therapy and dose-flexibility because they may be filled into a capsule, thereby allowing administration of specifically tailored dosage amounts or drug cocktails for personalized patient therapy. Mini-tablets facilitate the simultaneous administration of non-compatible drugs (i.e. drugs that can't otherwise be formulated together). Mini-tablets may include immediate release, delayed release, and/or controlled release formulations. Due to increased surface area in relation to volume, a drug can be released more efficiently from mini-tablets compared to traditional tablets.

Mini-tablets are especially promising for use in pediatric populations because a smaller tablet is more likely to be acceptable to children. Studies have found that mini-tablets are a potential dosage form suitable for 2-6 year olds (based on placebo tablets 3 mm in diameter). (Thomson, S. A. et al., *Pediatrics,* 2009; 123: e235-e8.) Other studies have found that very young children (6-12 months) were fully capable of swallowing mini-tablets of 2 mm diameter and that they often preferred them to sweet liquid formulations. (Spomer, N., et al., *Arch. Dis. Child.,* 2012; 97:283-86.) As used herein, a "pediatric patient" or "pediatric subject" means a human between 2 and 18 years of age.

In an embodiment of the present invention, the mini-tablets include an active pharmaceutical ingredient and one or more pharmaceutically acceptable carriers that are formulated so as to provide controlled-release of the active pharmaceutical ingredient according to a desired pharmacokinetic and pharmacodynamics profile. As used herein, the term "mini-tablet" means a flat or slightly curved pharmaceutical tablet having a diameter ranging between about 1.0 and 4.0 mm.

According to an embodiment of the present invention, the mini-tablets contain melatonin as an active ingredient. The melatonin may be present in a therapeutically effective amount, from about 1.0% to about 20.0% by weight of the total weight of the mini-tablet. In certain embodiments, the therapeutically effective amount of the active pharmaceutical ingredient in each mini-tablet is about 1 to about 10 mg, e.g., 1 mg, 2 mg, 3 mg, 4 mg, 5 mg, 6 mg, 7 mg, 8 mg, 9 mg or 10 mg. Melatonin analogs which substantially imitate the function of melatonin in the human body can be used in place of melatonin in the formulations and methods of the present invention. Such analogs include ramelteon, agomelatine, tasimelteon, β-methyl-6-chloromalatonin and TK-301. Other acceptable analogs are known to persons of skill in the art and include those listed in Depreux et al., *J. Med. Chem.* 37:3231-3239 (1994).

According to an embodiment of the present invention, the mini-tablets may contain one or more pharmaceutically acceptable carriers. Suitable carriers include, for example, diluents, lubricants, binders, glidants, anti-adherents, and other excipients. Suitable carriers include lactose, calcium hydrogen phosphate and acrylic resin carriers such as those produced under the name EUDRAGIT® by Rohm Pharmaceuticals in Darmstadt, Germany. In addition to the above ingredients, pharmaceutical grade magnesium stearate/stearic acid as a glidant, talc as an anti-adherent and colloidal silica as a lubricant may be included in the mini-tablet. The mini-tablets of according to the present disclosure may also contain one or more of ammonio methacrylate copolymer, calcium hydrogen phosphate dihydrate, lactose monohydrate. The ammonio methacrylate copolymer may be ammonio methacrylate copolymer type A (U.S. Pharmacopeia #1029909) or ammonio methacrylate copolymer type B (U.S. Pharmacopeia #1029910) or any other polymer providing the desired controlled release profile. In some embodiments, the mini-tablets according to the present invention include a fast dissolving sugar or alcohol that is not lactose, e.g., mannitol, sorbitol, erythritol, xylitol, dextrose, sucrose.

In some embodiments, the ratio between melatonin, ammonio methacrylate copolymer, calcium hydrogen phosphate dihydrate, and lactose monohydrate in the mini-tablet may be 1:1.1-5.9:0.8-8.3:1.8-8.8 by weight. In other embodiments, the ratio between melatonin, ammonio methacrylate copolymer, calcium hydrogen phosphate dihydrate, and lactose monohydrate in the mini-tablet may be 1:1.175:0.85:1.865. In further embodiments, the ratio between melatonin, ammonio methacrylate copolymer, calcium hydrogen phosphate dihydrate and lactose monohydrate in the mini-tablet may be 1:5.88:8.25:8.75 by weight.

The drug-release profile is strongly affected by formulation parameters and may be measured by in vitro dissolution of melatonin from mini-tablets in distilled water at 37° C. The type and amount of release-controlling agent (usually polymer) used in mini-tablets similarly determines the drug-release patterns mainly by diffusion. The instant inventors found that, in matrix mini-tablet studies, increasing the amount of rate-controlling compound led to slower drug release, which may be due to the increased hydrophobicity of the system. It was discovered that increasing water-insoluble compounds (e.g., lactose) provides faster drug release due to their water solubility and drug diffusion promotion.

Mini-tablet production is similar to the production of standard tablets, but requires excellent powder flow due to the small dies. Mini-tablet production also requires exact control of process parameters and special caution during tablet press assembly in order to avoid tool damage. The present inventors discovered that it was not possible to use known information about Circadin® tablets to make a priori assumptions or predictions about the resultant flowability, dissolution and release characteristics of mini-tablet formulations. In addition, the present inventors discovered that it was not possible to use known information about a developed mini-tablet dosage form, e.g., the first melatonin mini-tablet, to make a priori assumptions or predictions about the resultant flowability, dissolution and release characteristics of a mini-tablet having a different dosage amount, e.g., a second mini-tablet.

The mini-tablets of the instant invention may be provided as compressed tablets. The compressed mini-tablets may be prepared using the process of direct compression. In the direct compression method of tablet production, dry ingredients are thoroughly mixed and then compressed into tablets. The process of direct compression is convenient and cost-effective. However, the process is highly influenced by the characteristics of the active pharmaceutical ingredient (API) as well as the excipients, including flowability, compressibility and compatibility. Excipients must be selected carefully, because the raw materials must demonstrate good flowability and compaction properties for successful operation. Good powder flowability is necessary in terms of providing uniform die filling and for production of mini tablets with acceptable weight and content uniformity.

In order to improve flowability of the API/excipients powder, dry granulation via slugging or roller compaction can be employed. Dry granulation is used for increasing the bulk density of powders, whilst increasing the particle size, resulting in better flowing material, which is a prerequisite for manufacturing tablets on high speed production equipment. Bonding the particles of various substances together during the compaction process reduces the tendency for segregation of powder particles of different substances. This results in an improvement of the homogeneity of the active ingredients (API) within the powder blend, causing an improvement of dose uniformity of such dosage forms.

In some embodiments, the mini-tablets are coated. The type of coating process used usually depends on the type of coating material to be applied, whereas the durability of the tablet core depends both on the coating material and application process. Generally, one of the following types of coating procedures are used in the pharmaceutical industry: sugar coating, film coating, compression coating, and enteric coating.

The mini-tablets of the instant invention may be provided as a pharmaceutical controlled-release formulation comprising melatonin in combination with at least one pharmaceutical carrier, diluent or coating, wherein, upon administration to a patient, the formulation releases melatonin over time such that the patient's melatonin plasma profile substantially simulates the melatonin plasma profile of a human having a normal endogenous melatonin profile.

The mini-tablet may be administered to a patient who has trouble sleeping, or who suffers from a melatonin deficiency or distortion in comparison to a person with a normal endogenous plasma melatonin profile. The patient may be, for example, a pediatric patient, a geriatric patient, a disabled patient, a patient who has an autism spectrum disorder, a patient who has a neurogenetic disease, or a patient who has been diagnosed with dysphagia (difficulty swallowing).

As used herein, a "geriatric patient" or "geriatric subject" means a human of greater than 65 years of age.

A melatonin mini-tablet of the instant invention can be administered to a patient, for example, once or twice daily at preselected times, in order to raise the level of melatonin in the patient's blood to a desired level. In a preferred embodiment, the melatonin mini-tablet is administered so that the amount of melatonin in the patient's blood will substantially simulate the normal plasma melatonin night time profile, as shown in FIG. 1. Preferably, the mini-tablet will be administered before sleep, so that the desired profile will be achieved while the patient sleeps. Optionally, the melatonin mini-tablet may be administered between a first sleep period, such as before bedtime, and a second sleep period, such as during a period of waking in the middle of the night. In some embodiments, a first mini-tablet may be administered before a first sleep period, and a second mini-tablet may be administered between the first sleep period and a second sleep period. The first mini-tablet and the second mini-tablet may contain different amounts of melatonin.

In other embodiments the melatonin mini-tablet may be administered several hours before the desired bedtime to reset the biological clock in subjects suffering from transient or chronic circadian rhythms disorders (for example jet lag following trans meridian flight, sleep following night shift, clock resetting in totally blind individuals with non-24 h sleep wake disorder, delayed sleep phase syndrome).

In certain embodiments, melatonin mini-tablets are administered in combination with a substance which alters the phase position or shape of the patient's melatonin plasma profile, such as a melatonin receptor modifier or a melatonin profile modifier. As melatonin is known to act at a specific time of day and be ineffective at other times of the day due to diurnal variations in melatonin receptors, it is important that melatonin and its receptors be present simultaneously. Melatonin receptor modifiers include short-acting benzodiazepines, such as oxazepam and triazolam; melatonin profile modifiers include benzodiazepines, such as alprazolam (McIntyre, et al., *Chronobiology International*, 10:205-213 [1993]), beta-blockers, such as propranolol (Brismar et al., *Acta Medica Scandinavia*, 223:525 [1988]), serotonin uptake inhibitors, such as desipramine (Franey et al., *British J. Med. Pharmacol.*, 22:73 [1986]), acetylcholesterase inhibitors (Wong, C. W., *Drugs Aging*, 33(7):451-60 [2016]), and alpha antagonists, such as clonidine (Lewy et al., *J. Pharmaceutics and Pharmacology*, 38:55 [1986]).

In certain embodiments, the melatonin mini-tablets can be administered in combination with light therapy. Light can be used to adjust a patient's biological clock. In addition, a patient who has insufficient exposure to light may have internal desynchronization of his bodily rhythms, which may result in melatonin being produced during the daytime rather than at night. In such cases, treatment only with melatonin will not be fully satisfactory, as the patient also will have melatonin in his blood during the daytime. Light is known to suppress melatonin production by the pineal gland, so in these circumstances light can be used to help blunt melatonin production during the day. Exposure to light during the daytime can be continued until the patient's biological clock stabilizes. Thus, in accordance with the present invention, it would be desirable to encourage exposure to light during the day and avoidance of light at night.

Various Embodiments of the Invention Comprise

1. A controlled-release melatonin mini-tablet comprising: a therapeutically effective amount of melatonin; and one or more pharmaceutically acceptable carriers; wherein the mini-tablet has a diameter of less than or equal to 4 mm and has a release profile of less than 50% melatonin release within 1 hour, and about greater than 70% melatonin release within 6 hours.

1. The controlled-release melatonin mini-tablet of embodiment 1, wherein the therapeutically effective amount of melatonin is 1 mg.

3. The controlled-release melatonin mini-tablet of embodiment 1, wherein the therapeutically effective amount of melatonin is 2 mg.

4. The controlled-release melatonin mini-tablet of embodiment 1, wherein the therapeutically effective amount of melatonin is 3 mg.

5. The controlled-release melatonin mini-tablet of embodiment 1, wherein the therapeutically effective amount of melatonin is 4 mg.

6. The controlled-release melatonin mini-tablet of embodiment 1, wherein the therapeutically effective amount of melatonin is 5 mg.

7. The controlled-release melatonin mini-tablet of any of embodiments 1 to 6, wherein the mini-tablet is formulated such that it produces a minimal blood level of about 60 to about 200 picograms melatonin per milliliter over at least four hours after oral ingestion of the controlled-release melatonin mini-tablet by a human patient.

8. The controlled-release melatonin mini-tablet of any of embodiments 1 to 7, wherein the mini-tablet is formulated such that it produces a minimal blood level of about 100 to about 200 picograms melatonin per milliliter over at least four hours after oral ingestion of the controlled-release melatonin mini-tablet by a human patient.

9. The controlled-release melatonin mini-tablet of any of embodiments 1 to 8, wherein the mini-tablet contains one or more of the ammonio methacrylate copolymer, calcium hydrogen phosphate dihydrate, lactose monohydrate.

10. The controlled-release melatonin mini-tablet of any of embodiment 9, wherein the ammonio methacrylate copolymer is ammonio methacrylate copolymer type A.

11. The controlled-release melatonin mini-tablet of embodiment 9, wherein the ammonio methacrylate copolymer is ammonio methacrylate copolymer type B.

12. The controlled-release melatonin mini-tablet of embodiments 9, 10 and 11, wherein the ratio between melatonin, amino methacrylate copolymer, calcium hydrogen phosphate dihydrate and lactose monohydrate by weight is 1:1.1-5.9:0.8-8.3:1.8-8.8.

13. The controlled-release melatonin mini-tablet of any of embodiments 1 to 12, wherein the mini-tablet comprises a fast dissolving sugar or alcohol that is not lactose.

14. The controlled-release melatonin mini-tablet of any of embodiments 1 to 32, wherein the mini-tablet is coated with a pharmaceutically acceptable coating.

15. A method of manufacturing a controlled-release melatonin mini-tablet, the method comprising: combining a therapeutically effective amount of melatonin and one or more pharmaceutically acceptable carriers to produce a mixture; and compressing the mixture into mini-tablets that each have a diameter of less than or equal to 4 mm such that the mini-tablet has a controlled-release profile of less than 50% melatonin released within 1 hour of dissolution, and about greater than 70% melatonin released within 6 hours of dissolution.

16. The method of embodiment 15, further comprising a step of coating the tablets with a pharmaceutically acceptable coating.

17. The method of embodiment 15 or 16, wherein the combining step comprises dry blending the therapeutically effective amount of melatonin and the one or more pharmaceutically acceptable carriers.

18. The method of any of embodiments 15, 16, or 17, wherein the one or more pharmaceutically acceptable carriers comprise a fast dissolving sugar or alcohol that is not lactose.

19. The method of any of embodiments 15 to 18, wherein the pharmaceutically acceptable carriers comprise one or more of calcium hydrogen phosphate dihydrate, ammonio methacrylate copolymer, and lactose monohydrate.

20. A method of inducing sleep in a patient in need thereof, the method comprising: orally administering the controlled-release mini-tablet of embodiment 1 to the patient; wherein sleep is induced in the patient.

21. The method of embodiment 20, wherein the patient is a pediatric patient.

22. The method of embodiment 20, wherein the patient is a geriatric patient.

23. The method of any of embodiments 20 to 22, wherein the therapeutically effective amount is 1 mg.

24. The method of any of embodiments 20 to 22, wherein the therapeutically effective amount is 2 mg.

25. The method of any of embodiments 20 to 22, wherein the therapeutically effective amount is 3 mg.

26. The method of any of embodiments 20 to 22, wherein the therapeutically effective amount is 4 mg.

27. The method of any of embodiments 20 to 22, wherein the therapeutically effective amount is 5 mg.

28. The method of any of embodiments 20 to 27, wherein the mini-tablet comprises one or more of the calcium hydrogen phosphate dihydrate, ammonio methacrylate copolymer, and lactose monohydrate.

29. The method of any of embodiments 20 to 28, wherein the tablet is administered before sleep.

30. The method of any of embodiments 20 to 29, wherein the tablet is administered between a first sleep period and a second sleep period.

31. A method of orally administering melatonin to a patient who has difficulty swallowing tablets, the method comprising: orally administering the controlled-release mini-tablet of embodiment 1 to the patient.

32. The method of embodiment 31, wherein the therapeutically effective amount is 1 mg.

33. The method of embodiment 31, wherein the therapeutically effective amount is 2 mg.

34. The method of embodiment 31, wherein the therapeutically effective amount is 3 mg.

35. The method of embodiment 31, wherein the therapeutically effective amount is 4 mg.

36. The method of embodiment 31, wherein the therapeutically effective amount is 5 mg.

37. The method of any of embodiments 31 to 36, wherein the mini-tablet comprises one or more of the calcium hydrogen phosphate dihydrate, ammonio methacrylate copolymer and lactose monohydrate.

38. A method of inducing a phase shift of the circadian rhythm of a patient in need thereof, the method comprising: orally administering the controlled-release mini-tablet of embodiment 1 to the patient; wherein a phase shift in the patient's circadian rhythm is induced in the patient.

39. A method of safely inducing and maintaining sleep in a patient in need thereof, the method comprising: providing a pharmaceutical product comprising one or more melatonin mini-tablets capable of inducing sleep in a patient and achieving a minimal blood level of about 60 to about 200 picograms melatonin per milliliter over at least four hours following the administration without inducing unacceptable side effects in a human, wherein said pharmaceutical product is manufactured by combining a therapeutically effective amount of melatonin and one or more pharmaceutically acceptable carriers to produce a mixture, compressing the mixture into one or more mini-tablets that each have a diameter of less than or equal to 4 mm such that the mini-tablet has a release profile of less than 50% melatonin release within 1 hour, and about greater than 70% melatonin release within 6 hours, and optionally filling a plurality of the mini-tablets into a capsule; and orally administering the one or more mini-tablets to the patient.

40. A pharmaceutical mini-tablet formulation comprising melatonin in combination with at least one pharmaceutical carrier, diluent or coating, wherein, upon administration to a patient, the mini-tablet formulation releases melatonin over time such that the patient's melatonin plasma profile substantially simulates the melatonin plasma profile of a human having a normal endogenous melatonin profile.

41. Use of a controlled-release melatonin mini-tablet for therapy, the controlled-release melatonin mini-tablet comprising a therapeutically effective amount of melatonin; and one or more pharmaceutically acceptable carriers; wherein the mini-tablet has a diameter of less than or equal to 4 mm and has a release profile of less than 50% melatonin release within 1 hour, and about greater than 70% melatonin release within 6 hours.

42. Use of a controlled-release melatonin mini-tablet in a method of inducing sleep in a patient in need thereof, the controlled-release melatonin mini-tablet comprising a therapeutically effective amount of melatonin; and one or more pharmaceutically acceptable carriers; wherein the mini-tablet has a diameter of less than or equal to 4 mm and has a release profile of less than 50% melatonin release within 1 hour, and about greater than 70% melatonin release within 6 hours.

43. Use of a controlled-release melatonin mini-tablet in a method of inducing a phase shift of the circadian rhythm of a patient in need thereof, the controlled-release melatonin mini-tablet comprising a therapeutically effective amount of melatonin; and one or more pharmaceutically acceptable carriers; wherein the mini-tablet has a diameter of less than or equal to 4 mm and has a release profile of less than 50% melatonin release within 1 hour, and about greater than 70% melatonin release within 6 hours.

44. Use of a controlled-release melatonin mini-tablet in a method of safely inducing and maintaining sleep in a patient in need thereof, the controlled-release melatonin mini-tablet comprising a therapeutically effective amount of melatonin; and one or more pharmaceutically acceptable carriers; wherein the mini-tablet has a diameter of less than or equal to 4 mm and has a release profile of less than 50% melatonin release within 1 hour, and about greater than 70% melatonin release within 6 hours.

The present invention is illustrated by the following examples, which are not intended to be limiting.

EXAMPLES

Example 1—Development of a First Melatonin Mini-Tablet

The inventors sought to develop a first melatonin mini-tablet. 2 mg controlled-release melatonin tablets (about 8 mm diameter) were commercially available under the brand name Circadin®, and the inventors initially attempted to use the formulation of Circadin® to develop the first melatonin mini-tablets. The commercial Circadin® formulation contains a specific combination of ammonio methacrylate copolymer type B, calcium hydrogen phosphate dihydrate, and lactose monohydrate. The formulation of Circadin® is described in U.S. Pat. No. 6,469,044, which is incorporated herein by reference in its entirety. The 2 mg Circadin® formulation is also shown in Table I, below.

The inventors initially attempted to prepare a melatonin mini tablet by direct compression using the same inactive ingredients as those used in commercial Circadin® 2 mg. However, it was impossible to use the Circadin® formulation to produce a melatonin mini-tablet because an unacceptable difference in melatonin release rate was recognized. Specifically, decreasing the tablet size from the standard level (8 mm) to mini-level (≤4 mm) resulted in unacceptably fast drug release due to increased surface-to-volume ratio. Additionally, the Circadin® tablet was produced using wet granulation, and required the use of an organic solvent as a granulation liquid, causing health, safety, disposition and residual level issues. Accordingly, it was necessary to develop a completely novel formulation and manufacturing process in order to produce mini-tablets that could achieve the same pharmacokinetic and pharmacodynamic properties as the Circadin® tablet.

Various formulations for the melatonin mini-tablet were produced by dry blending. Initially, the tablets were formulated with decreased ratios of lactose monohydrate and an increased ratio of calcium hydrogen phosphate dihydrate when compared to Circadin® 2 mg. These mini-tablets demonstrated promising dissolution profiles, but were still outside the Circadin® 2 mg dissolution specification.

In subsequent studies, two additional lots were prepared using an increased amount of calcium hydrogen phosphate (55.5% by weight), and 12% or 15% by weight of ammonio methacrylate copolymer type B, respectively. These variations were made in an attempt to slow down the dissolution profile of the first melatonin formulation. Mini-tablets containing 35% lactose and about 33% of calcium hydrogen phosphate gave optimal results with a dissolution profile falling between the low and high limit dissolution specifications. Table I shows the ratio of ingredients (by weight) in the first melatonin mini-tablet formulation, in comparison to the Circadin® formulation.

TABLE I

| | Melatonin | Calcium Hydrogen Phosphate Dihydrate | Ammonio Methacrylate Copolymer, Type B or A | Lactose |
|---|---|---|---|---|
| First Minitab | 1 | 8.25 | 5.87 | 8.75 |
| 2 mg Circadin | 1 | 20 | 20 | 40 |

Example 2—Development of a Second Melatonin Mini-Tablet

In order to produce an acceptable second melatonin mini-tablet, it was necessary to design, manufacture and test at least 10 different formulations. The initial formulations were based on the first mini-tablet formulation shown in Table I. Table II presents seven different tablet formulations (Ex. 1-Ex. 7), for which the proportions of calcium hydrogen phosphate dihydrate, ammonio methacrylate copolymer, and lactose monohydrate were varied in order to obtain adequate physical mini-tablet properties, and to obtain acceptable dissolution profiles.

For the first formulation (Ex. 1), the increased amount of melatonin was compensated for by reducing the amount of calcium hydrogen phosphate. However, the compressed tablets revealed a dissolution profile which was too slow compared to the target profile.

Lactose monohydrate is a fast-release agent. Based on the assumption that the hydrophilic lactose will increase the dissolution rate, a second prototype (Ex. 2) was manufactured with an increased amount of lactose. In order to compensate for the increased lactose, the amount of ammonio methacrylate copolymer type B was decreased, while calcium hydrogen phosphate was kept the same as the first prototype. The dissolution profile of tablets of the second prototype was surprisingly too slow.

After the confirmation that higher lactose in the second prototype increased the dissolution rate, the third prototype (Ex. 3) was manufactured with a maximum amount of lactose. To compensate for the increased amount of lactose, the amount of ammonio methacrylate copolymer type B and calcium hydrogen phosphate was reduced. Testing of this third prototype revealed that the dissolution profile of the mean values complied with the target dissolution profile of the first mini-tablet formulation. However, there was an unacceptably high variability among the tested samples (8 tabs).

Assuming that the high variability of the third prototype was due to incomplete matrix formation, the fourth prototype (Ex. 4) was prepared with an increased amount of ammonio methacrylate copolymer type B. This increase was compensated for by a decrease in calcium hydrogen phosphate. Testing of this fourth prototype showed that the mean dissolution rate was unacceptably slow and did not meet the target specifications.

In an attempt to get a formulation with a faster dissolution rate, a fifth prototype (Ex. 5) was manufactured. While the component combinations were similar to the second formulation, a different quality of lactose, having a smaller particle size, was used. Testing the fifth prototype revealed that the particle size of lactose did not influence the dissolution of melatonin. Accordingly, it was necessary to design and test further prototypes. Sixth and seventh prototypes (Ex. 6 and Ex. 7) were manufactured using a more permeable grade of ammonio methacrylate copolymer (type A). The sixth and seventh prototypes were based on the first and second prototypes, respectively. The dissolution profiles of the sixth and seventh prototypes were acceptable.

TABLE II

|  | Ex. 1 | Ex. 2 | Ex 3 | Ex. 4 | Ex. 5 | Ex. 6 | Ex. 7 |
| --- | --- | --- | --- | --- | --- | --- | --- |
| Melatonin | 1 | 1 | 1 | 1 | 1 | 1 | 1 |
| Type of Ammonium Methacrylate | B | B | B | B | B | A | A |
| Ammonio Methacrylate | 1.17 | 0.78 | 0.6 | 0.8 | 0.8 | 1.18 | 0.78 |
| Calcium Hydrogen Phosphate | 0.85 | 0.85 | 0.6 | 0.4 | 0.4 | 0.85 | 0.85 |
| Lactose Monohydrate | 1.75 | 2.15 | 2.58 | 2.58 | 2.58 | 1.75 | 2.15 |

Example 3—Human Clinical Trial

The effect of prolonged-release (PR) melatonin mini-tablets according to the present invention was determined in a study population consisting of randomized 125 Children with Autism Spectrum Disorder (ASD) and/or neurogenetic diseases. The children were screened and entered a 4 weeks sleep hygiene period, those who did not respond to the non-pharmacological treatment continued into a single blind placebo run-in for 2 weeks; those who were still eligible after these 2 weeks, were randomized to receive either 2 mg active treatment (2× 1 mg PR melatonin mini-tablet) or placebo for 3 weeks. After these 3 weeks those who did not respond to the treatment were escalated to a dose of 5 mg (5× 1 mg PR melatonin mini-tablet) in both treatment groups for another 10 weeks double blind period (altogether 13 weeks double blind treatment period). After this period, children continued for a 13 week open label period on the dose that they took up to that point.

Sleep parameters were measured by a Daily Sleep and Nap Diary that was completed by the parents 2 weeks before each visit. For each subject, the mean sleep variable was calculated as the mean of the last 14 days prior to each scheduled visit; the change from baseline in mean variable was analyzed using a mixed-effects model for repeated-measures (MMRM).

It was found that the PR melatonin mini-tablet significantly improved total sleep time over placebo after 3 months (SE=standard error) as shown in Table III.

TABLE III

| | Adjusted treatment mean sleep variable (SE) | | | |
| --- | --- | --- | --- | --- |
| | PR melatonin mini-tablets (N = 58) | Placebo (N = 61) | Treatment difference (SE) | p-value |
| Week 15 | 56.16 (10.46) | 18.73 (10.82) | 32.43 (15.10) | 0.034 |

It was also found that PR melatonin MT significantly improved sleep initiation (SL) over placebo after 3 months as shown in Table IV.

TABLE IV

| | Adjusted treatment mean sleep initiation (SE) | | | |
|---|---|---|---|---|
| | PR melatonin mini-tablets (N = 58) | Placebo (N = 61) | Treatment difference (SE) | p-value |
| Week 15 | −37.88 (6.82) | −12.58 (7.00) | −25.30 (9.79) | 0.011 |

Conclusion: PR melatonin mini-tablets treatment improves sleep in ASD children suffering from sleep disturbances by shortening sleep initiation and improving sleep maintenance.

All citations (e.g., scientific journal publications, patents, and other reference material) mentioned herein are hereby incorporated herein by reference to the same extent as if each individual citation was specifically and individually indicated to be incorporated by reference.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The foregoing summary, description, examples and drawings of the invention are not intended to be limiting, but are only exemplary of the inventive features which are defined in the claims.

The invention claimed is:

1. A controlled-release melatonin mini-tablet comprising:
   1 mg or 5 mg melatonin; and
   one or more pharmaceutically acceptable carriers;
      wherein the mini-tablet has a diameter of less than or equal to 4 mm and has a release profile of less than 50% melatonin release within 1 hour, and about greater than 70% melatonin release within 6 hours of oral ingestion by a human patient,
      wherein the mini-tablet contains ammonio methacrylate copolymer, calcium hydrogen phosphate dihydrate, lactose monohydrate, and
      wherein the ratio between melatonin, ammonio methacrylate copolymer, calcium hydrogen phosphate dihydrate and lactose monohydrate by weight is 1:1.1-5.9:0.8-8.3:1.8-8.8.

2. The controlled-release melatonin mini-tablet of claim 1, wherein the mini-tablet is formulated such that it produces a minimal blood level of about 60 to about 200 picograms melatonin per milliliter or about 100 to about 200 picograms melatonin per milliliter over at least four hours after oral ingestion of the controlled-release melatonin mini-tablet by a human patient.

3. The controlled-release melatonin mini-tablet of claim 1, wherein the ammonio methacrylate copolymer is ammonio methacrylate copolymer type A.

4. The controlled-release melatonin mini-tablet of claim 1, wherein the ammonio methacrylate copolymer is ammonio methacrylate copolymer type B.

5. The controlled-release melatonin mini-tablet of claim 1, wherein the mini-tablet comprises a fast dissolving sugar or alcohol that is not lactose.

6. The controlled-release melatonin mini-tablet of claim 1, wherein the mini-tablet is coated with a pharmaceutically acceptable coating.

7. A pharmaceutical mini-tablet formulation comprising 1 mg or 5 mg melatonin in combination with at least one pharmaceutical carrier, diluent or coating, wherein, upon administration to a patient, the mini-tablet formulation releases melatonin over time such that the patient's melatonin plasma profile substantially simulates the melatonin plasma profile of a human having a normal endogenous melatonin profile,
   wherein the mini-tablet contains ammonio methacrylate copolymer, calcium hydrogen phosphate dihydrate, lactose monohydrate, and
   wherein the ratio between melatonin, ammonio methacrylate copolymer, calcium hydrogen phosphate dihydrate and lactose monohydrate by weight is 1:1.1-5.9:0.8-8.3:1.8-8.8.

* * * * *